United States Patent
Albert

(10) Patent No.: US 12,263,003 B2
(45) Date of Patent: *Apr. 1, 2025

(54) MOBILE CARDIAC MONITORING AND ANALYSIS

(71) Applicant: AliveCor, Inc., Mountain View, CA (US)

(72) Inventor: David E. Albert, Oklahoma City, OK (US)

(73) Assignee: ALIVECOR, INC., Mountain View, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 17/827,478

(22) Filed: May 27, 2022

(65) Prior Publication Data

US 2022/0287613 A1    Sep. 15, 2022

Related U.S. Application Data

(63) Continuation of application No. 17/277,266, filed as application No. PCT/US2019/050069 on Sep. 6, 2019, now Pat. No. 11,344,244.

(60) Provisional application No. 62/732,496, filed on Sep. 17, 2018.

(51) Int. Cl.
*A61B 5/327* (2021.01)
*A61B 5/00* (2006.01)
*A61B 5/28* (2021.01)

(52) U.S. Cl.
CPC ............... *A61B 5/327* (2021.01); *A61B 5/28* (2021.01); *A61B 5/681* (2013.01); *A61B 5/6898* (2013.01)

(58) Field of Classification Search
CPC ............ A61B 5/327; A61B 5/28; A61B 5/681
See application file for complete search history.

(56) References Cited

U.S. PATENT DOCUMENTS

| | | |
|---|---|---|
| 2005/0192503 A1 | 9/2005 | Sula et al. |
| 2010/0076331 A1 | 3/2010 | Chan et al. |
| 2012/0059271 A1 | 3/2012 | Amitai et al. |

(Continued)

FOREIGN PATENT DOCUMENTS

| | | |
|---|---|---|
| JP | 2016521164 A | 7/2016 |
| JP | 2016530896 A | 10/2016 |

(Continued)

OTHER PUBLICATIONS

International Search report for International application No. PCT/US2019/050069, mailed Nov. 29, 2019.

*Primary Examiner* — Paula J Stice
(74) *Attorney, Agent, or Firm* — Womble Bond Dickinson (US) LLP

(57) ABSTRACT

Described herein are devices, systems, and methods for sensing, generating, and time aligning one or more of the 12 leads of a standard ECG. A set of electrodes may be used to perform an electrocardiogram (ECG) of a user to generate a set of limb leads including a first lead I. A Wilson's Central Terminal (WCT) value may be determined using a subset of the set of limb leads. In response to an electrode of the set of electrodes contacting the user's chest, a precordial lead may be generated based on electric potentials sensed by the electrode while contacting the user's chest and the WCT value. As the precordial lead is generated, a corresponding second lead I is simultaneously generated. The corresponding second lead I is used to time align the set of limb leads and the precordial lead.

20 Claims, 10 Drawing Sheets

(56) References Cited

U.S. PATENT DOCUMENTS

| | | |
|---|---|---|
| 2013/0172723 A1 | 7/2013 | Baxi et al. |
| 2014/0228665 A1 | 8/2014 | Albert |
| 2015/0018660 A1 | 1/2015 | Thomson et al. |
| 2016/0287172 A1 | 10/2016 | Paulsen et al. |
| 2017/0127966 A1 | 5/2017 | Wu et al. |
| 2018/0271392 A1 | 9/2018 | Saldivar |

FOREIGN PATENT DOCUMENTS

| | | |
|---|---|---|
| WO | 2014172451 A1 | 10/2014 |
| WO | 2016161228 A1 | 10/2016 |

MOBILE CARDIAC MONITORING AND ANALYSIS

RELATED APPLICATIONS

This application is a continuation of U.S. patent application Ser. No. 17/277,266, filed Mar. 17, 2021 and entitled "MOBILE CARDIAC MONITORING AND ANALYSIS," now issued as U.S. Pat. No. 11,344,244 on May 31, 2024, which is a National Stage Entry of PCT/US2019/050069 filed on Sep. 6, 2019, which claims the benefit under 35 U.S.C. § 119(e) of U.S. Provisional Patent Application No. 62/732,496 filed on 17 Sep. 2018, the entire contents of which are hereby incorporated by reference herein.

BACKGROUND

It is estimated that by 2030, over 23 million people will die from cardiovascular diseases annually. Cardiovascular diseases are prevalent in the populations of high-income and low-income countries alike. Monitoring of cardiovascular function will aid in the treatment and prevention of cardiovascular disease.

The mammalian heart generates and conducts an electric current that signals and initiates the coordinated contraction of the heart. In humans, an electric signal is produced by a portion of the heart known as the SA node. After being generated by the SA node, the electric current travels throughout the myocardium in a manner that is predictable in a healthy heart.

In general, an electrocardiogram (ECG) is a graphic representation of the electric conduction of the heart over time as projected on the surface of the body. An ECG is typically displayed on a graph having an x and y axis. Typically, the x-axis of an ECG displays time and the Y-axis of an ECG displays the electric potential (in millivolts) of an electric current that is conducted through the heart during normal cardiac function.

SUMMARY

Described herein are ECG sensing devices, systems, and methods for sensing and analyzing an ECG of an individual. In some embodiments, the devices, systems, and methods described herein comprise a mobile computing device including, for example, a smartphone and/or a wearable computing device. In some embodiments, the mobile computing device comprises a housing, a display screen, a memory, and a processor, wherein the processor is coupled to the display screen and the memory. Non-limiting examples of mobile computing devices suitable for use with the systems, devices, and methods described herein include smartphones, smartwatches, tablet computers, and laptop computers.

The ECG sensing devices, systems, and methods described herein include one or more electrodes coupled to a housing and a processor for measuring an electric potential on a skin surface of an individual. In some embodiments, the devices, systems, and methods described herein include three electrodes each of which is positioned on any surface of the mobile computing device: The first electrode is configured to sense a first electric potential on a skin surface of a left upper extremity of the individual, the second electrode is configured to sense a second electric potential on a skin surface of a right upper extremity of the individual, and the third electrode is configured to sense a third electric potential on a skin surface of a left lower extremity of the individual.

Described herein is a device for sensing and analyzing an electrocardiogram (ECG), comprising: a mobile phone or a wearable computing device having a first electrode positioned on any surface of the mobile phone or the wearable computing device, a second electrode positioned on any surface of the mobile phone or the wearable computing device, and a third electrode positioned on any surface of the mobile phone or the wearable computing device, and wherein the mobile phone or wearable computing device comprises: a processor; and a non-transitory computer readable storage medium encoded with a computer program including instructions executable by the processor that causes the processor to: sense an ECG comprising three limb leads and three augmented limb leads using the first electrode, the second electrode, and the third electrode; determine a Wilson's Central Terminal (WCT) value using two or more of the three limb leads; and sense one or more of the precordial leads using any one of the first electrode, the second electrode, and the third electrode, wherein the one or more precordial leads comprise a difference between an electric potential sensed by either the first electrode, the second electrode, or the third electrode and the WCT value. In some embodiments, the computer program causes the processor to determine a QRS axis. In some embodiments, the computer program causes the processor to determine a QRST angle. In some embodiments, the computer program causes the processor to: receive an electric potential value from the one or more of the first electrode, the second electrode, and the third electrode when the one or more of the first electrode, the second electrode, and the third electrode is positioned over an anterior chest of an individual, and wherein the one or more precordial leads that is sensed comprise a difference between the electric potential and the WCT value. In some embodiments, the computer program causes the processor to generate an average waveform for each of the three limb leads, an average waveform for each of the three augmented limb leads, and an average waveform for the one or more precordial limb leads. In some embodiments, the computer program causes the processor to time align the average waveform for each of the three limb leads, the average waveform for each of the three augmented limb leads, and the average waveform of the one or more precordial leads. In some embodiments, the computer program causes the processor to display the three limb leads, the three augmented limb leads, and the one or more precordial leads in a time aligned format. In some embodiments, the wearable computing device comprises a smartwatch.

Described herein is a method for sensing and analyzing an ECG, comprising: sensing a limb lead and an augmented limb lead using an ECG sensing device comprising a mobile phone or wearable computing device comprising a first electrode, a second electrode, and a third electrode; determining a WCT value; and sensing a precordial lead comprising the difference between an electric potential sensed by any one of the first electrode, the second electrode, and the third electrode and the WCT value. In some embodiments, the computer program causes the processor to determine a QRS axis. In some embodiments, the computer program causes the processor to determine a QRST angle. In some embodiments, the computer program causes the processor to: receive an electric potential value from the one or more of the first electrode, the second electrode, and the third electrode when the one or more of the first electrode, the second electrode, and the third electrode is positioned over an anterior chest of an individual, and wherein the one or more precordial leads that is sensed comprise a difference between the electric potential and the WCT value. In some embodiments, the computer program causes the processor to generate an average waveform for each of the three limb leads, an average waveform for each of the three augmented limb leads, and an average waveform for the one or more precordial limb leads. In some embodiments, the computer program causes the processor to time align the average waveform for each of the three limb leads, the average waveform for each of the three augmented limb leads, and the average waveform of the one or more precordial leads. In some embodiments, the computer program causes the processor to display the three limb leads, the three augmented limb leads, and the one or more precordial leads in a time aligned format. In some embodiments, the wearable computing device comprises a smartwatch.

Also described herein is a method for displaying an ECG, comprising: sensing a first ECG waveform with an ECG sensing device comprising a smartphone or wearable computing device; generating either a first average ECG waveform or a first median ECG waveform from the first ECG waveform that was sensed; sensing a second ECG waveform with the ECG sensing device; generating either a second average ECG waveform or a second median ECG waveform from the second ECG waveform that was sensed; and displaying with the ECG sensing device either the first average ECG waveform or the first median ECG waveform together with either the second average ECG waveform or the second median ECG waveform, wherein either the first average ECG waveform or the first median ECG waveform is displayed in alignment with either the second average ECG waveform or the second median ECG waveform. In some embodiments, the wearable computing device comprises a smartwatch. In some embodiments, the first ECG waveform and the second ECG waveform are sensed at different times. In some embodiments, the first ECG waveform comprises either a limb lead or augmented limb lead. In some embodiments, the second ECG waveform comprises a precordial lead. In some embodiments, alignment comprises a vertical alignment of a first PQRST complex from either the first average ECG waveform or the first median ECG waveform and a second PQRST complex from either the second average ECG waveform or the second median ECG waveform.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows the front of the embodiment of an ECG device which comprises a display screen. FIG. 3B shows the embodiment of an ECG sensing device rotated 90 degrees.

FIG. 4A shows the embodiment of an ECG sensing device rotated 90 degrees. FIG. 4B shows the back of the ECG sensing device comprising three electrodes.

DETAILED DESCRIPTION

Figures 1A, 1B:
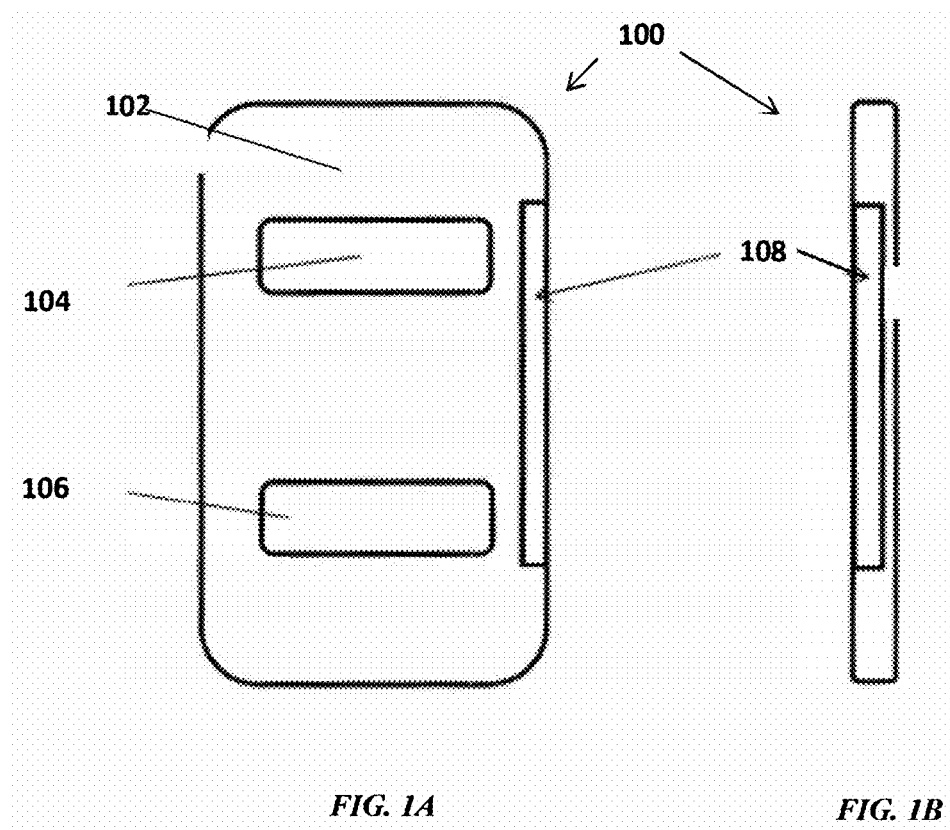
FIGS. 1A-1B show an exemplary tracing of a six lead ECG.

Described herein are devices, methods, and systems for sensing, displaying, and analyzing an ECG of an individual.
ECG Sensing In some embodiments of the systems, devices, and methods described herein, an ECG sensing device comprises a mobile computing device configured to sense one or more of ECG leads I, II, III, aVR, aVL, aVF, V1, V2, V3, V4, V5, and V6. In some embodiments, systems, devices, and methods described herein, ECG sensing device comprises less than the ten electrodes of a traditional ECG sensing device. In some embodiments of the ECG sensing device, the device comprises 3 electrodes that are configured to sense one or more of ECG leads I, II, III, aVR, aVL, aVF, V1, V2, V3, V4, V5, and V6.

In some embodiments, an ECG sensing device as described herein senses six ECG leads, which are leads I, II, III, aVR, aVL, and aVF. In some embodiments, an ECG sensing device as described herein senses twelve ECG leads, which are I, II, III, aVR, aVL, aVF V1, V2, V3, V4, V5, and V6. An ECG sensing device as described herein comprising three electrodes is configured to sense six leads or twelve leads.

Lead I is typically a waveform representing the electric potential difference between the left arm (LA) and the right arm (RA) as expressed by the relationship lead I=LA−RA.

Lead II is typically a waveform representing the electric potential difference between the right arm and left leg (LL) as expressed by the relationship lead II=LL−RA.

Lead III is typically a waveform representing the electric potential difference between the left leg and left arm as expressed by the relationship lead III=LL−LA.

Lead aVR is typically a waveform representing the electric potential difference between the right arm and a composite of the left arm and left leg as expressed by the relationship aVR=RA−½(LA+LL).

Lead aVL, is typically a waveform representing the electric potential difference between the left arm and a composite of the right arm and left leg as expressed by the relationship aVL=LA−½(RA+LL).

Lead aVF is typically a waveform representing the electric potential difference between the left leg and a composite of the left arm and right arm expressed by the relationship aVF=LL−½(LA+RA).

Leads aVR, aVL, and aVF are generated by an ECG sensing device or system from electric potential differences between one of RA, LA, and LL, and a composite comprising of two of RA, LA, and LL. Thus, three electrodes positioned at RA, LA, and LL will sense aVR, aVL, and aVF simultaneously based on the above relationships. Which is to say that while leads, I, II, and III each require input from only two electrodes, and aVR, aVL, and aVF require input from three electrodes positioned at RA, LA, and LL.

A standard named composite pole is known as Wilson's Central Terminal (WCT). WCT may be expressed by the relationship WCT=⅓(RA+LA+LL).

Leads V1, V2, V3, V4, V5, and V6 are unipolar leads and as such each uses a position on the chest as its positive pole and WCT as its negative pole. The positions on the chest at which an electrode is placed for the purposes of measuring V1, V2, V3, V4, V5, and V6 are standardized with regard to a user's anatomy. The positive pole of V1 is typically measured in the fourth intercostal space just to the right of the sternum. The positive pole of V2 is typically measured in the fourth intercostal space just to the left of the sternum. The positive pole of V3 is typically measured between leads V2 and V4. The positive pole of V4 is typically measured in the fifth intercostal space in the mid-clavicular line. The positive pole of V5 is typically measured horizontally even with V4, in the left anterior axillary line. The positive pole of V6 is typically measured horizontally even with V4 and V5 in the midaxillary line.

In a three electrode ECG sensing device, RA serves as the reference electrode for lead I and lead II so that it can be taken to be zero (i.e. assumed to represent zero). As such, lead I can be expressed as lead I=LA−0 or lead I=LA and lead II can be expressed as lead II=LL−0 or lead II=LL.

Taking RA=0 in a three electrode ECG sensing device, WCT may be expressed as (lead I+lead II)/3.

Taking RA=0 in the three electrode ECG sensing device, aVR may be expressed as—(lead I−lead II)/2, aVL=lead I−(lead II/2), and aVF may be expressed as lead II−(lead I/2).

Figure 2:
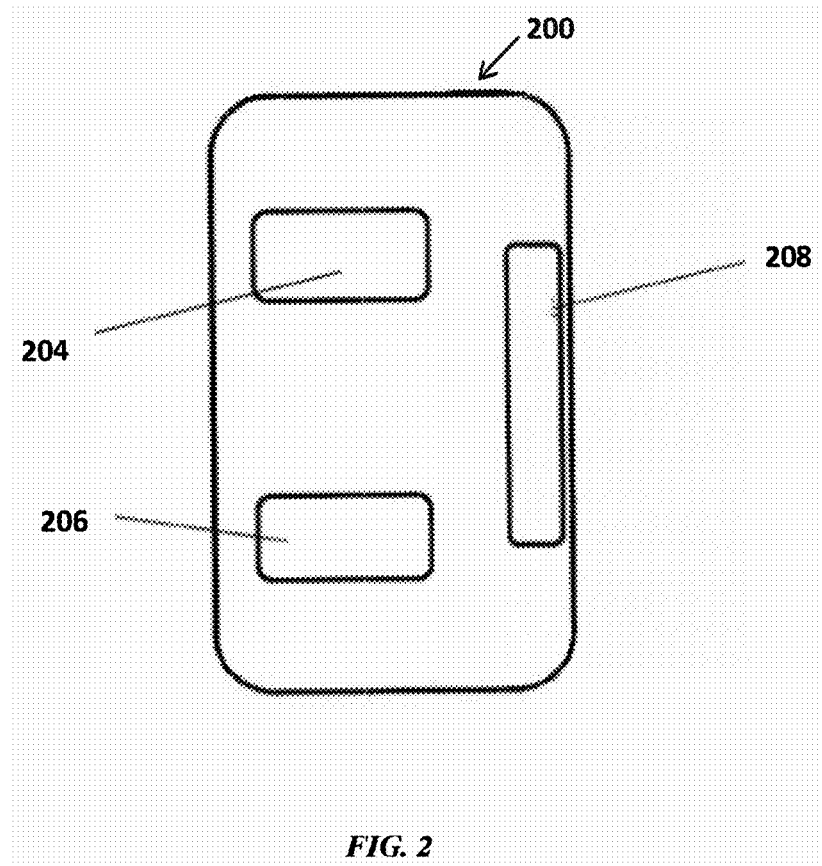
FIG. 2 shows an exemplary front view of an embodiment of an ECG sensing device.
Figure 3:
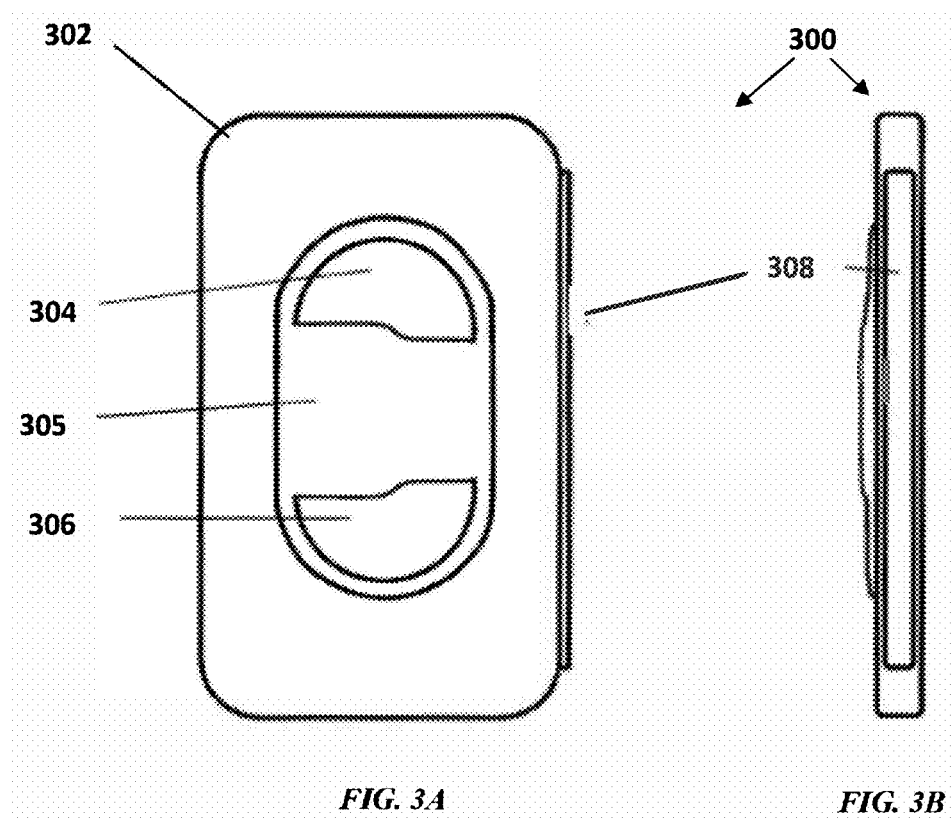
FIGS. 3A-3B respectively show posterior and side views of ECG sensing device having three electrodes, wherein one or more electrodes are elevated above the surface of the device.

In some embodiments of the ECG sensing device described herein, an ECG sensing device comprises a mobile computing device along with three electrodes. FIGS. 1-3 show exemplary embodiments of ECG sensing devices wherein the mobile computing device comprises a smartphone, and also show exemplary arrangements of three electrodes relative to the smartphone.

FIGS. 1A-1B respectively show a posterior view and a side view of an exemplary embodiment of an ECG sensing device 100. In this embodiment, the ECG sensing device 100 comprises a mobile computing device 102 along with three electrodes 104, 106, and 108. In some embodiments, as shown in FIGS. 1A-1B, a mobile computing device 102 comprises a smartphone. It should, however, be understood that other mobile computing devices such as, for example, smartwatches, tablet computers, and laptop may be configured together with electrodes 104, 106, and 108 as shown in FIGS. 1A-1B.

FIG. 1A shows a posterior view of the ECG sensing device 100. A first electrode 104 and a second electrode 106 are positioned on the back surface of the ECG sensing device 100.

FIG. 1B shows a third electrode 108 positioned along the side surface of the ECG sensing device (the device is rotated 170 degrees). As shown in FIG. 1B, in a rectangular shaped mobile device 102, such as a smartphone, a third electrode 108 is positioned on a side surface of the rectangular shape and may be positioned on any one of the four side surfaces. In general, the third electrode 108 is positioned so that when in contact with the left lower extremity of an individual, the ECG sensing device 100 is in a horizontal position so that substantially the entire length of the third electrode 108 is in contact with the left leg of an individual. First and second electrodes 104 and 106 are positioned in such a way that when third electrode 108 is in contact with the left lower extremity of a user, first electrode 104 and second electrode 106 may be naturally and comfortably contacted by an individual's right and left hands respectively while the user holds the ECG sensing device with a screen of the device 100 facing up so that the user of the device 100 may view the screen. In the embodiment shown in FIGS. 1A-1B, the first and second electrodes 104 and 106 are positioned on the back of the device 100 (i.e. the side of the device opposite the screen).

Additionally, in this and similar embodiments, the first and second electrodes 104 and 106 are spaced far enough apart from one another that an individual would not easily contact the wrong electrode or more than one electrode at once when holding the device with display facing them and the first and second electrodes 104 and 106 being obscured from view by the device 100.

When the device is positioned so that the third electrode 108 is in contact with the left lower extremity of a user, the user may simultaneously contact electrode 104 with their right hand and contact electrode 106 with their left hand all while comfortably looking at a screen of the mobile computing device 102. For example, the user may sit in a chair with their left leg crossed over their right leg and hold electrode 108 against their left leg (e.g. at the ankle) while contacting electrode 104 with their right hand and electrode 106 with their left hand. In particular, it is the placement of electrode 108 along the side surface of the ECG sensing device 100 that facilitates the apparatus to be used such that a measurement from the left leg is taken while viewing a surface (e.g., the screen) of the mobile computing device 102.

As shown, the ECG sensing device 100 comprises a mobile computing device 102 and first, second, and third electrodes 104, 106, and 108. In some embodiments, the first, second, and third electrodes 104, 106, and 108 may be recessed within the housing of the ECG sensing device 100. In some embodiments of the device 100, one or more of electrodes 104, 106, and 108 are integral with a mobile computing device 102. For example, one or more of the electrodes 104, 106, and 108 may be integral with a housing of a mobile computing device housing. In some embodiments, of the ECG sensing device 100, one or more of the first, second, and third electrodes 104, 106, and 108 may be detachable from the mobile computing device 102.

It should be understood that in other similar embodiments, an ECG sensing device as described herein comprises an alternative mobile computing devices 102, such as, for example, a smartwatch, a tablet, or a laptop. In embodiments, comprising alternative mobile computing devices, similar positioning of the electrodes 104, 106, and 108 may be achieved as shown with respect to the mobile computing device 102 shown in FIG. 1.

FIG. 2 shows another embodiment of an ECG sensing device 200 having three electrodes 204, 206, and 208, wherein all three electrodes are positioned on the back of the device. In this embodiment, all three electrodes 204, 206, and 208 are positioned on the back of the ECG sensing device 200 such that they are separated sufficiently to allow a user to comfortably contact all three simultaneously without inadvertently contacting more than one electrode with the same body part.

FIGS. 3A-3B respectively show posterior and side views of an exemplary embodiment of an ECG sensing device 300 comprising a mobile computing device 302 comprising a smartphone, and wherein one or more of a first, second, and third electrodes 304, 306, and 308 are positioned on a surface of a base unit 305 that is configured to reversibly couple with the smartphone such that ECG sensing device 300 comprises a smartphone coupled to the base unit 305. In the embodiments shown in FIGS. 3A-3B, the base unit 305 comprises first and second electrodes 304 and 306 while 308 is not a part of the base unit 305.

In some embodiments, the base unit comprises first, second, and third electrodes 304, 306, and 308. In some of these embodiments, the base unit 305 is configured and/or positioned so that first, second, and third electrodes 304, 306, and 308 are positioned as shown in FIGS. 3A-3B with first and second electrodes 304 and 306 positioned on the posterior surface of the ECG sensing device 300 and third electrode 308 on a side surface of the ECG sensing device 300.

In some embodiments of the ECG sensing device 300, a base unit 305 is integral with a smartphone case. In some embodiments, a base unit 305 removably couples with a smartphone case. For example, a smartphone case comprises an opening fitted to receive a base unit 305, and each of the smartphone case and base unit 305 having couplers configured to reversibly couple the base unit 305 with the smartphone case. In some embodiments, a removably coupleable base unit 305 comprising first, second, and third electrodes 304, 306, and 308 may be interchangeably couplable with more than one type of case. For example, said base unit may couple with a plurality of different types of cases configured to couple with a plurality of devices. In some embodiments, a base unit 305 is configured to couple directly with a mobile computing device 300, using, for example, an adhesive surface or other coupling mechanism.

Figure 4:
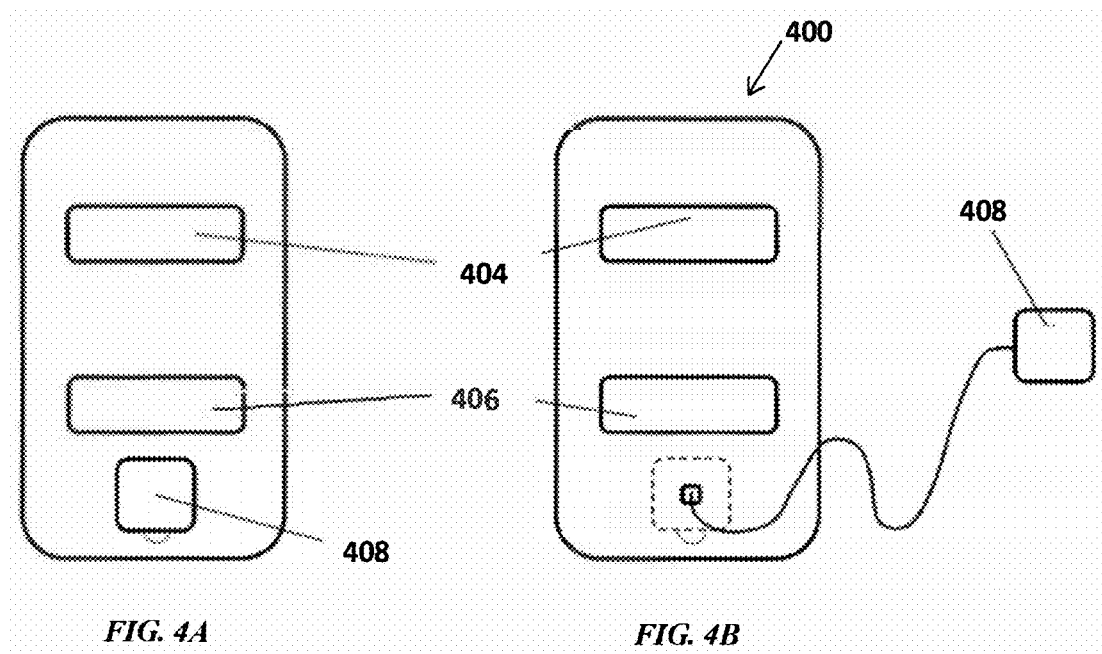
FIGS. 4A-4B show multiple views of another embodiment of an ECG sensing device having three electrodes, wherein an electrode is positioned partially on the side surface of the device and partially on the back surface of the device.

FIGS. 4A-4B show posterior views of an embodiment of an ECG sensing device 400 having an external retractable electrode 408 that extends from the housing on a wire (shown retracted in 4B). When not in use, the wire may be retracted into the ECG sensing device 400 and the electrode 408 may be coupled to the case. When in use, the retractable electrode 408 may be pulled from the case and may, for example, contact the patient's leg, so that the case and smartphone may be held and viewed by the patient. In some embodiments, a third electrode 408 is detachable from the ECG sensing device 400 and is configured to transmit a wireless signal to the ECG sensing device when detached comprising an ECG signal. It should be understood, that one or more of a first and/or second electrode 404 and 406 may also be configured in other embodiments to either be retractable with a wire or detachable with wireless communication capability.

In any of the above described embodiments, the mobile computing device may provide visual feedback to the user before or during the recording. For example, a display of a mobile computing device may indicate to the user that good electric contact is being made, and/or showing the ECGs sensed.

Figure 5:
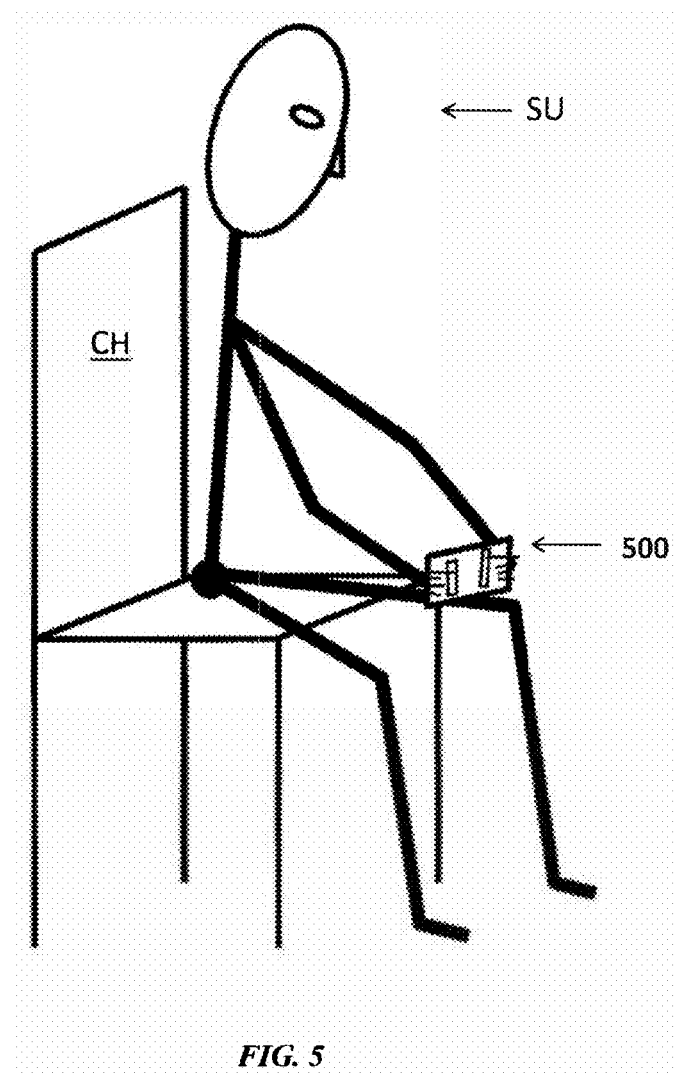
FIG. 5 shows an embodiment of an ECG sensing device having three electrodes, wherein all three electrodes are positioned on the back of the device.

FIG. 5 shows an illustration of an exemplary method of operating an ECG sensing device 500 having three electrodes as described herein. In this example, the user SU is sitting in a chair CH and holds the apparatus 500 with both hands so that each hand contacts just one electrode on the back of the case. The case is held against the user's left leg so that an electrode is pressed against the left leg of the user. In some embodiments, one or more capacitive electrodes are used in the ECG sensing device 500 so that, for example, the capacitive electrode senses an electric potential through a garment worn over the left lower extremity of the user. Similarly, a conductive spray or gel is placed on the left lower extremity of the user so that a typical electrode senses an electric potential through a garment worn over the left lower extremity of the user. The case and smartphone may then be used to record Lead I, Lead II, and Lead III, from which at least three additional leads may be determined, as described herein. Specifically, the augmented leads, aVR, aVL, and aVF, may be determined using Leads I, II, and III.

While not shown in FIG. 5, an individual may also record the precordial leads V1, V2, V3, V4, V5, and V6 using a three electrode ECG sensing device 500 as described herein. The device 500 is configured so that an individual holds an electrode with one of each of his left and right hands and holds the third electrode sequentially against the six electrode positions on the chest described herein corresponding to leads V1, V2, V3, V4, V5, and V6. In some embodiments, while the user holds an electrode of the device 500 with each of his right and left hands and simultaneously holds the third electrode of the device 500 against a positon on his chest corresponding to V1, V2, V3, V4, V5, and V6, each of the electric potentials sensed at the chest positions corresponding to V1, V2, V3, V4, V5, and V6 are sensed simultaneously with an electric potential sensed at LA and RA. Lead I is equivalent to the potential difference between LA and RA. Thus, in some embodiments, measuring an electric potential at a position on the chest corresponding to any of V1, V2, V3, V4, V5, and V6 together with the electric potential at the LA and RA positions is equivalent to the difference in potential at the chest position and lead I. That is, for example, using all three electrodes of device 500 as described, V1 (the electric potential at the V1 chest position)=("CP1")−WCT (WCT=(RA+LA+LL)/3 or (lead I+lead II)/3).

The six precordial chest positions can be represented as ("CP1," "CP2," "CP3," "CP4," "CP5," and "CP6") and a composite value known as Wilson's Central Terminal ("WCT").

"CP(x)" corresponds to any of the six potentials sensed at the anatomical precordial lead positions (where "x" is a position number 1-6). For example, CP1 is the ECG measurement sensed at a location at which an electrode is placed to measure V1, and that position is approximately in the second intercostal space immediately to the right of the sternum. Thus, lead V1=CP1−WCT.

WCT is equal to one third of the sum of the potentials sensed at the right upper extremity, left upper extremity, and left lower leg or ⅓(RA+LA+LL). In a standard ECG that uses ten simultaneously placed electrodes, a WCT value is generated at the same time that a precordial lead is sensed, because RA, LA, LL, which determine WCT, are sensed at the same time as CPI, CP2, CP3, CP4, CP5, and CP6.

An ECG sensing device as described herein comprises at least three electrodes, but typically less than the ten standard electrodes. In some embodiments of the ECG sensing device described herein, the device comprises three electrodes. In these embodiments, the electrodes are positioned and configured to simultaneously sense the six limb leads I, II, III, aVR, aVL, and aVF when a user contacts a first electrode with a right upper extremity, a second electrode with a left upper extremity, and a third electrode with a left lower extremity.

As also described herein, an ECG sensing device is configured to sense the six leads V1, V2, V3, V4, V5, and V6 sequentially when a user, for example, contacts a first electrode with a right upper extremity, a second electrode with a left upper extremity, and a third electrode with an area of his or her chest corresponding to a precordial lead position.

In some embodiments of the ECG sensing device comprising three electrodes described herein, RA, LA, LL, which determine WCT, are not sensed simultaneously with one or more precordial leads. That is, when one of the three electrodes of the ECG sensing device is held against the chest wall of a user, only two electrodes remain free and a traditional WCT cannot be simultaneously determined. In some of these embodiments, RA is set to 0. When RA=0, it provides a WCT=(0+LA+LL)/3 or ((LA−0)+(LL−0))/3 which can be further expressed as WCT=(lead I+lead II)/3.

Likewise, in these embodiments, wherein RA is set to 0, an averaged WCT=(averaged lead I+averaged lead II)/3. An averaged WCT in some embodiments is generated using an averaged lead I and an averaged lead II that are generated using, for example, an ensemble averaging method on the lead I and lead II waveforms sensed by the ECG sensing device described herein. Generating an average WCT is beneficial in, for example, signal filtering and also simplifies alignment of values for purposes of subtraction. That is, in some embodiments, CPI, CP2, CP3, CP4, CP5, and CP6 are each averaged and an averaged WCT is respectively subtracted from each to generate V1, V2, V3, V4, V5, and V6.

In this manner, a three lead ECG sensing device 500 is used to sense a 12-lead ECG. In a first step an individual holds a first electrode with a left hand a second electrode with a right hand and presses a third electrode against their left leg to simultaneously generate leads I, II, III, aVR, aVL, and aVF. In a second step the user holds a first electrode with a left hand, a second electrode with a right hand, and a third electrode against the six precordial lead positions in order to sense leads V1, V2, V3, V4, V5, and V6.

In some embodiments, a software program on the ECG sensing device 500 displays or otherwise transmits instructions to an individual instructing the user as to how to position the electrode over the standard precordial lead chest positions. For example, a display may show an image of a location on the user's chest against which the user is instructed to hold the third electrode while holding electrodes one and two with his left and right hands respectively.

In some embodiments, software on the ECG sensing device 500 is configured to recognize if a first electrode is contacted by a left hand and second electrode is being contacted by a right hand versus whether a first electrode is contacted by a right hand a second electrode is contacted by a left hand. For example, in some embodiments, a third electrode is positioned on a different surface of the ECG sensing device 500 than the first and second electrodes, such that a user will likely need to turn the ECG sensing device 180 degrees to contact the precordial lead positions on their chest with the third electrode after contacting their left leg with the third electrode. As such, when the ECG sensing device 500 is rotated 180 degrees in space, the first and second electrodes will rotate so that a user will end up holding the first electrode with a left hand originally and then a right hand when the device is rotated and similarly will hold a second electrode with a right hand originally and then a left hand when the device is rotated. In some embodiments, software on the ECG sensing device 500 receives information from a sensor coupled with or integrated with an ECG sensing device 500, wherein the sensor provides information about the position of the device in space. Examples of the class of sensors that sense such information include but are not limited to accelerometers, inclinometers, and gyrometers.

In some embodiments, the ECG sensing device 500 is configured to sense an ECG when one or more of the sensors are not engaged by the user. For example, in some embodiments, an ECG sensing device 500 comprises three electrodes, and the ECG sensing device 500 is configured to sense an ECG when either all three electrodes are engaged by the user or when any two of the three electrodes are engaged by the user. That is, in this embodiment, when a user, for example, contacts a skin surface on their right upper extremity with a first electrode and contacts a skin surface on their left upper extremity with a second electrode, but does not contact the third electrode, the ECG sensing device senses an ECG. When, in this example, the two of three electrodes are contacted by a right and left upper extremity respectively, a lead I is sensed. Likewise, when the two of three electrodes are contacted by a right upper extremity and left lower extremity respectively, a lead II is sensed. Likewise, when the two of three electrodes are contacted by a left upper extremity and left lower extremity respectively, a lead III is sensed. In this embodiment, the ECG sensing device 500 recognizes that one or more of the electrodes have not been contacted by a user while two or more electrodes have been contacted by the user, by, for example, sensing an electrode potential from two or more electrodes that are contacted but not sensing an electrode potential from electrodes that are not contacted by the user.

Aberrant cardiac conduction may be visualized on an ECG recording, because aberrant cardiac conduction will produce an abnormal ECG recording. An abnormal ECG may indicate cardiac function and structure abnormalities associated with cardiac disease. For example, various abnormal rhythm patterns on ECG are indicative of arrhythmias such as, for example, atrial fibrillation. For example, a deviation in axis on an ECG may indicate ventricular hypertrophy. For example, changes in the ECG waveform such as, for example, ST elevation may indicate acute myocardial infarction.

Figure 6:
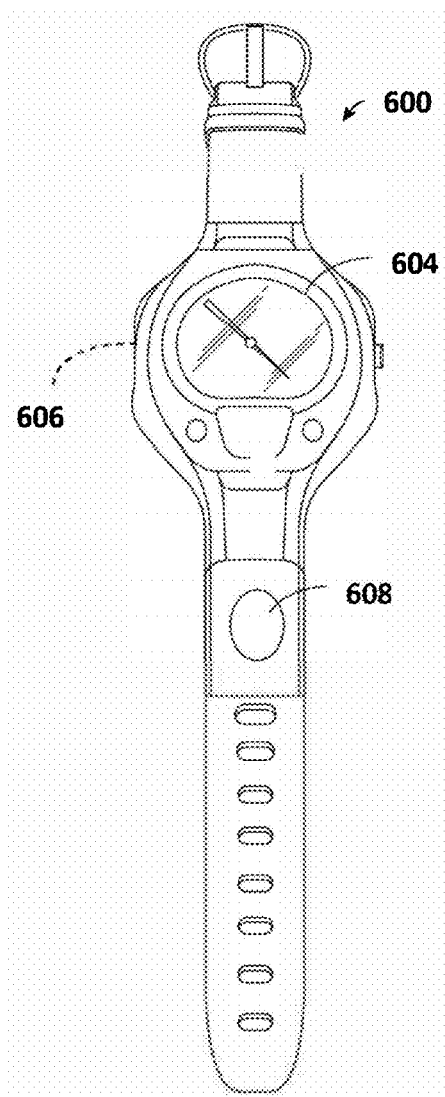
FIG. 6 shows an embodiment of an ECG sensing device having three electrodes, wherein electrode is positioned partially on the side surface of the device and partially on the back surface of the device, and wherein electrode is elevated above the back and side surfaces of the device.

FIG. 6 shows an embodiment of an ECG sensing device 600 comprising a wristlet comprising a smartwatch. In this embodiment, a smartwatch may comprise an ECG sensing device 600 which may further comprise three electrodes. As shown in FIG. 6, a first electrode 604 is positioned on the front surface of the watch and may, for example, be positioned on the face of ECG sensing watch. A second electrode 606 (not shown) is positioned on the back surface of the watch so that it is continuously in contact with the skin of a user when the watch is worn. A third electrode 608 may be positioned on the front of the ECG sensing watch, for example, on a watch wristband or strap. From this positon on the watch, it is convenient for a user to contact electrode 608 with the left lower extremity of the user. The watch may also include one or more controls and/or indicators. For example, the watch may also be configured as a timepiece (showing the time, etc.). The watch may include buttons, dials, etc. to select functions (e.g., turning on/off ECG reading, to begin to transmit ECG information, etc.). An ECG sensing watch may comprise a display on its face that displays a recorded ECG. It should be understood, that method illustrated in FIG. 5 may be modified for use with the ECG sensing device shown in FIG. 6, wherein a user simultaneously contacts the first, second, and third electrodes 604, 606, and 608 of the watch, to sense leads I, II, III, aVR, aVL, and aVF (and WCT), and then contacts the third electrode 608 to the six precordial lead positions to sense CP1, CP2, CP3, CP4, CP5, and CP6, while also contacting at least one of the first and second electrodes 604 and 606 thus generating V1, V2, V3, V4, V5, and V6.

Figure 7:
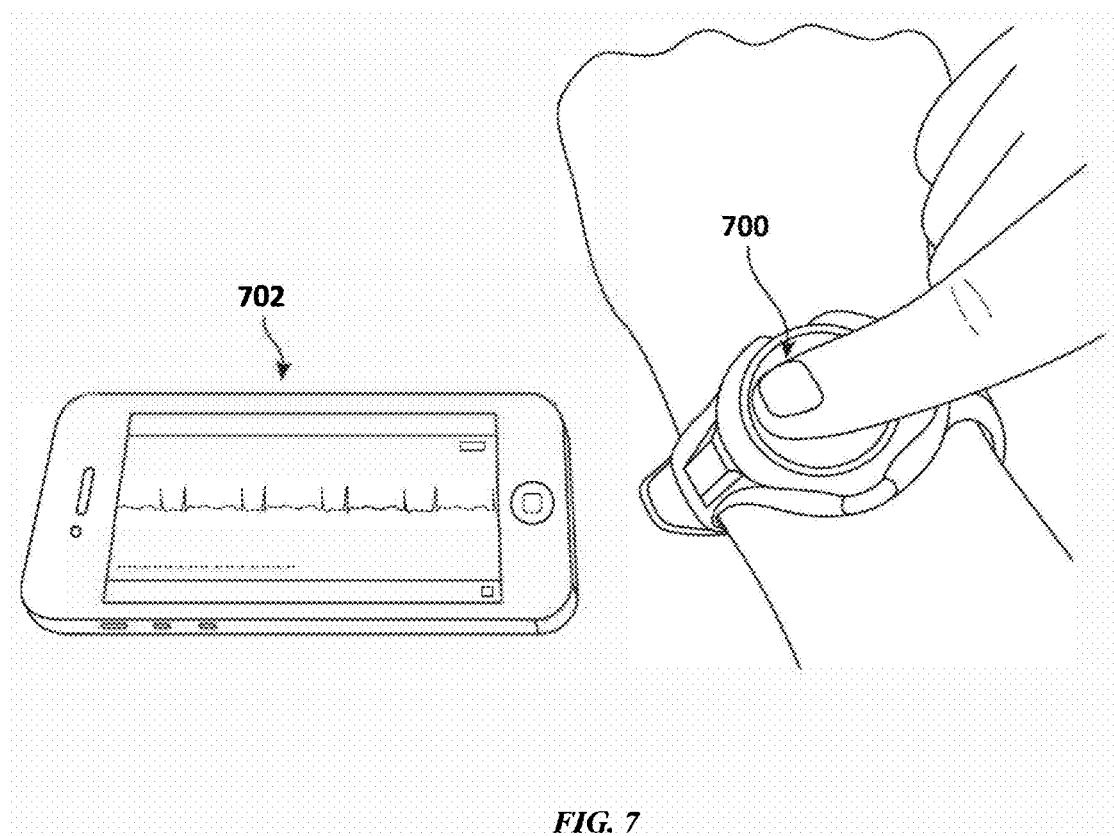
FIG. 7 shows an embodiment of an ECG sensing device, wherein three embodiments are positioned on a surface of a smartphone case that is coupled with mobile computing device such that ECG sensing device comprises a smartphone coupled to a smartphone case.

FIG. 7 shows an embodiment of a wristlet ECG sensing device 700 that is configured to communicate with mobile computing device 702. In this embodiment, the ECG sensing device 700 comprises two or more electrodes positioned to conveniently be contacted by a left upper extremity, a right upper extremity, and a left lower extremity (in the three electrode embodiment) of a user. A mobile computing device 702 comprises a smartphone that is configured to act as the receiving station for the ECG sensing device 700, and receive wireless transmission of ECG information from ECG sensing watch 700. A wireless transmission may comprises, for example, a WiFi connection between the ECG sensing watch 700 and the mobile computing device 702, a BlueTooth connection between the ECG sensing watch 700 and the mobile computing device 702, a low power BlueTooth connection between the ECG sensing watch 700 and the mobile computing device 702, an NFC (near field communication) connection between the ECG sensing watch 700 and the mobile computing device 702, or a near field ultrasound communication connection between the ECG sensing watch 700 and the mobile computing device 702. Thus, the smartphone 702 is running application software so that the processor of the smartphone causes a receiver that is sensitive to a wireless signal to 'listen' for such signals transmitted from the ECG sensing watch. The receiving device (smartphone) 702 may then process the received signal and display, in real-time as shown in FIG. 7, the ECG signals as they are being recorded on the ECG sensing watch 700. In this example, the smartphone 702 is continuously receiving, displaying and recording the signal.

As mentioned, the signal may be processed by either the ECG sensing watch or the mobile computing device before being displayed and/or stored and/or transmitted. For example, the signal may be filtered to remove artifacts and/or smooth. The signal may also be analyzed to automatically detect cardiac events (e.g., arrhythmias). Processing may be performed prior to ultrasound transmission by the watch, after transmission to a receiving device by the receiving device (e.g., smartphone) or divided between both.

In some embodiments, an ECG sensing watch may determine or confirm that a receiving device (e.g., smartphone) is ready to receive the information, as discussed above.

In some embodiments, half- or full-duplex may be used. The watch may continuously broadcast the ECG data, or it may only transmit upon indication that the receiver is ready to receive; in such variations the ECG sensing watch or the mobile computing device may store detected ECG data for later transmission.

In the embodiments shown in FIGS. 6 and 7, either the ECG sensing watch or the mobile computing device is also configured to determine heart rate data from the ECG that is sensed. Additional information may also be extracted from the ECG that is sensed.

As mentioned above, the signal may be transmitted by the device (e.g., wristlet) as digital, analog or hybrid digital/analog wireless signals. Further, the signals may be encoded; in some variations, the device includes a key that can be scanned by the smartphone to provide decryption/pairing between the smartphone (receiver) and the device as discussed above.

Although many of the exemplary devices described herein are wearable devices (e.g., wristlets, watches, chest bands, pendants, jewelry, etc.) the principles, modules, sub-systems, and elements described herein may be used for other devices, particularly biological sensor devices. For example, a case or holder for a mobile telecommunications device (e.g., smartphone) may incorporate any of these aspects, such as encoding of the ultrasonic signal, encoding as a hybrid digital/analog wireless signal, or the like. Thus in addition to wearable medical sensors, any stand-alone medical sensor may also include any of these features.

In some embodiments of the ECG sensing devices described herein, exemplary embodiments of which are shown in FIGS. 1-7, a mobile computing device is configured to run a software application as described herein. In further embodiments, the mobile computing device includes one or more hardware central processing units (CPUs) or general purpose graphics processing units (GPGPUs) that carry out the device's functions. In still further embodiments, the mobile computing device further comprises an operating system configured to perform executable instructions. In some embodiments, the mobile computing device is optionally connected a computer network. In further embodiments, the mobile computing device is optionally connected to the Internet such that it accesses the World Wide Web. In still further embodiments, the mobile computing device is optionally connected to a cloud computing infrastructure. In other embodiments, the mobile computing device is optionally connected to an intranet. In other embodiments, the mobile computing device is optionally connected to a data storage device.

In accordance with the description herein, suitable mobile computing devices include, by way of non-limiting examples, server computers, desktop computers, laptop computers, notebook computers, sub-notebook computers, netbook computers, netpad computers, handheld computers, smartphone, smartwatches, digital wearable devices, and tablet computers.

In some embodiments, the mobile computing device includes an operating system configured to perform executable instructions. The operating system is, for example, software, including programs and data, which manages the device's hardware and provides services for execution of applications. Non-limiting examples of suitable operating systems include FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

In some embodiments, a mobile computing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the mobile computing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes, optical disk drives, and cloud computing based storage. In further embodiments, the storage and/or memory device is a combination of devices such as those disclosed herein.

In some embodiments, the mobile computing device includes a display to send visual information to a user. In some embodiments, the mobile computing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

In various embodiments, the platforms, systems, media, and methods described herein include a cloud computing environment. In some embodiments, a cloud computing environment comprises a plurality of computing processors.

It should be understood that FIGS. 1-7 show exemplary embodiments of the user matter described herein, and, generally, numerous electrode positions, shapes, and sizes may be used in the devices described herein so that an individual comfortably and naturally contacts the electrodes. For example, all three electrodes may be positioned entirely on the sides of a computing device or a device cover. For example, two electrodes on the back surface of the device may be positioned anywhere on the back surface of the computing device or cover including over the corners. Non-limiting examples of electrode shapes may comprise essentially flat rectangles, triangles, and circles as well as protruding three dimensional shapes such as polygons and spheroidal shapes. ECG sensing electrodes may comprise any suitable electric conducting material such as a conducting metal or alloy. Also, sensing electrodes may be comprised of capacitive devices.

In some embodiments, one or more electrodes are configured to be removable from the ECG sensing device. In these embodiments, for example, the ECG sensing device has either a male or female connector configured to snap-fit couple to a corresponding male or female connector on a removable electrode.

In any of the embodiments shown in FIGS. 1-7, one or more electrodes may be configured to be removable from the ECG sensing device. In these embodiments the ECG sensing device has, for example, either a male or female connector configured to snap-fit couple to a corresponding male or female connector on a removable electrode.

While the embodiments of FIGS. 1-7 show ECG sensing devices comprising three electrodes, it should be understood that the other numbers of ECG electrodes may be incorporated into the ECG sensing devices described herein. For example, a four electrode ECG sensing device may, for example, have a fourth electrode positioned along a side surface of a mobile computing device so that first and second electrodes are positioned on a posterior surface of a mobile computing device, a third electrode is positioned on a first side surface of the mobile computing device, and a fourth electrode is positioned on a second side surface of the mobile computing device. In similar fashion, five electrodes or six electrodes or seven electrodes or eight electrodes or nine electrodes or ten electrodes may also be used with an ECG sensing device in accordance with the teachings herein. Furthermore, any number of electrodes of an ECG sensing device as described herein may be retractable and/or detachable from the mobile computing device as, for example, illustrated in FIGS. 4A-4B.

In general, any of the techniques, components and/or subsystems described above may be use or combined with any of the other examples. For example, any of the ECG wristlet devices described herein may include any of the features mentioned above.

All of the devices described herein are suitable for use in various systems, which may include one or more servers, one or more sensors, an electronic data communication networks, as well as other ECG sensing devices. In some embodiments, a plurality of ECG sensing devices as described herein transmit ECG data to one or more remote servers through an electronic data communication network. In some embodiments, the ECG data is analyzed using the one or more remote servers. In some embodiments, arrhythmia detection is carried out using a remote server that analyzes received ECG data.

All of the devices and systems described herein may also include one or more software modules. In some embodiments, software comprises an app that is configured to run on a mobile computing device such as, for example, a smartphone, a smartwatch, or a tablet computer. The software receives and processes ECG data received from an ECG sensing device. The software identifies separate leads within the transmitted data, based on for example, which electrodes the ECG data originated from. For example, the software may be able to identify a lead I based on the signal originating from two electrodes that measure an electric potential difference between the right and left upper extremities. Once an ECG is identified, the software may further be configured to display a single or multi-lead ECG on a display screen of a mobile computing device. The software may be configured to display six leads I, II, III, aVR, aVL, and aVF simultaneously on a display screen. The software may be configured to display one or more of the six leads I, II, III, aVR, aVL, and aVF on a display screen at once, wherein a user is able to manually toggle screens to see a different lead or leads on different toggled screens.

The software modules described herein comprise computer readable and executable code. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Displaying a Sensed ECG

In a standard ECG waveform tracing, twelve ECG leads are displayed individually on an X and Y axis, wherein the Y-axis represents time and the X-axis represents voltage. In these tracings, all twelve ECG waveforms are aligned with respect to their X-axes. That is, the PQRST waveforms of all the leads all occur at the same time along the X-axis of each of the respective tracings. For example, in a traditional ECG waveform tracing, if a QRS complex occurs at 1 second on the X-axis in the lead I waveform tracing, a QRS complex occurs at 1 second in each of the other eleven ECG waveforms (i.e. leads II, III, aVR, aVL, aVF, V1, V2, V3, V4, V5, and V6).

The standard time aligned format allows health care providers to more easily obtain information from the twelve sensed ECG waveforms. In the traditional ECG tracing, time alignment is facilitated by virtue of the waveforms being sensed simultaneously by the ten electrodes of the traditional ECG that are all simultaneously positioned on the skin of the individual whose ECG is sensed. That is, because all twelve ECG leads of a traditional ECG are sensed simultaneously, time-alignment is achieved by simply displaying all of the waveforms together on identical axes.

Figure 8:
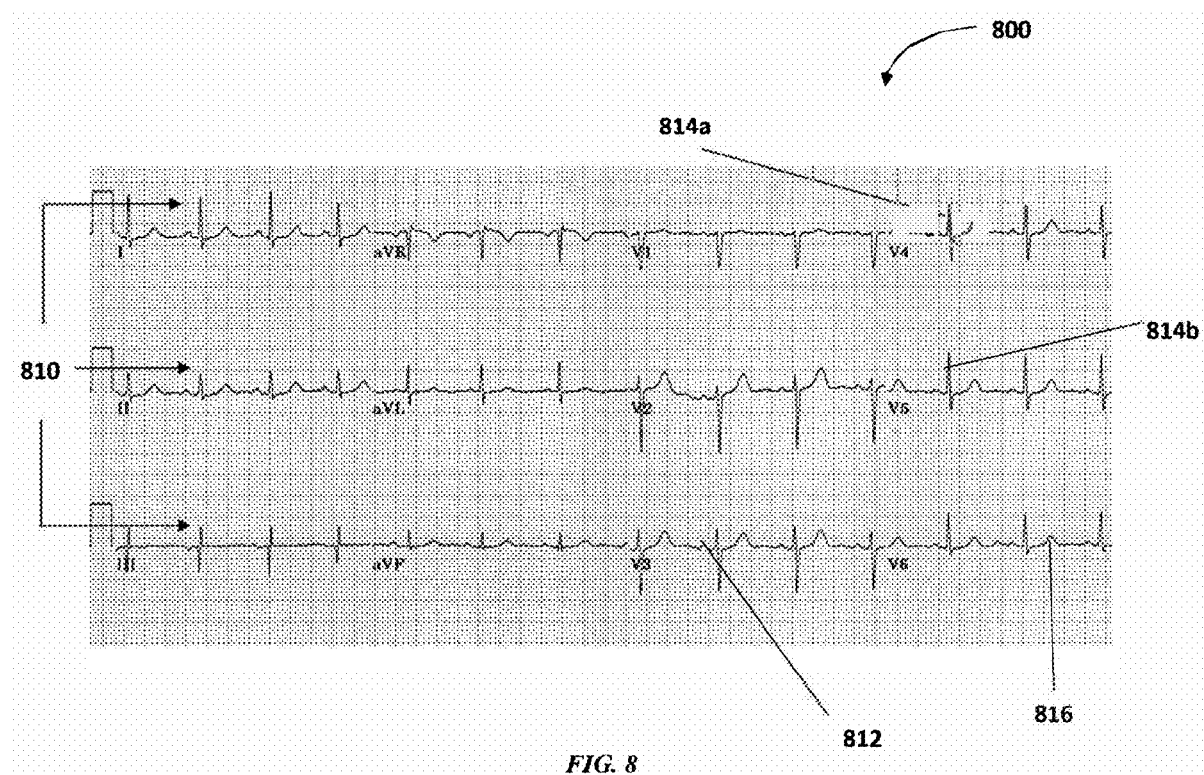
FIG. 8 shows an exemplary tracing of a twelve lead ECG

FIG. 8 shows an exemplary tracing of a twelve lead ECG 800 as is sensed by the devices, systems, and methods described herein. Each of the twelve displayed leads, I, II, III, aVR, aVL, aVF, V1, V2, V3, V4, V5, and V6 in the exemplary tracing shown in FIG. 8 represents the electric potential of the electric current passing through the heart from twelve different vantage points.

In this exemplary ECG tracing 800, the waveforms are time-aligned along the X-axis of the ECG. In a traditional ECG readout one or more individual waveforms are time aligned with one or more other individual waveforms so that the sensed waveforms can be conveniently compared by one viewing the ECG. As shown, ECG tracing 800 displays one or more waveforms in vertical alignment with one or more other waveforms. Aligned waveform tracings 810 show the waveforms of leads I, II, and III in vertical alignment with one another. Typically, each time aligned waveform corresponds to the same heartbeat.

Typically, an ECG of a normal beating heart has a predictable wave-form which can be seen in FIG. 8 in each of the twelve ECG leads. A typical ECG wave-form comprises a number of component parts or sections. The components of a typical ECG wave-form are referred to as P wave 812, QRS wave (or complex) 814, and T wave 816. Each wave or a complex of multiple waves (i.e. the QRS complex) is associated with a different phase of the hearts depolarization and repolarization. ECG portions between two waves are referred to as segments and ECG portions between more than two waves are referred to as intervals. For example, the ECG portion between the end of the S wave (part of QRS complex) and the beginning of the T wave 816 is referred to as the ST segment. For example, the portion of the ECG between the beginning of the Q wave (part of QRS complex) and the end of the T wave 816 is referred to as the QT interval.

An ECG 800 is generated by measuring electric potentials on different skin surfaces of the body of an individual using electrodes. Typically, a single ECG recording or lead corresponds to a difference in electric potential between two points on the body of an individual measured over time.

In some embodiments of the systems, methods, and devices described herein, two or more sensed leads that are not simultaneously sensed are time aligned to generate a time aligned ECG tracing displaying two or more leads in a time aligned format such as in a traditional standard twelve lead ECG tracing. In some embodiments of the ECG sensing device described herein, one or more ECG sensing electrodes are not simultaneously positioned on the skin of the individual whose ECG is sensed (i.e. some leads may be sequentially sensed). For example, the limb leads (I, II, III, aVR, aVL, and aVF) are simultaneously sensed while one or more of the precordial leads are sensed separately from the limb leads. As such, in these embodiments, the six limb leads are not automatically time aligned with the individually and separately sensed precordial leads and a further process is carried out by a software application to time align one or more of the limb leads with one or more of the precordial leads. In some embodiments, one or more of the six precordial leads are individually sensed so that the individually sensed precordial leads are time aligned by a software application with the six limb leads as well as with the other precordial leads. In some embodiments, a software application described herein aligns two or more sensed precordial leads with one another and separately time aligns six sensed limb leads so that two sets of six leads are respectively time aligned (i.e. six time aligned precordial leads and six separately time aligned limb leads). In some embodiments, the software described herein aligns two or more sensed precordial leads with one another as well as with sensed limb leads so that all twelve sensed leads are time aligned.

In some embodiments of the devices, systems, and methods described herein, one or more average or median waveforms are generated for a first and a second lead so that waveforms corresponding to different heartbeats are time aligned. That is, in some embodiments wherein one or more leads are not sensed concurrently, an average or median waveform is generated for one or more of these leads and the averaged or median waveforms are time-aligned so that the PQRST waveforms are aligned vertically along the X-axis (as shown in FIG. 8).

Time alignment of an ECG sensed with an ECG sensing device as described herein involves use of a software application that is configured to time align the PQRST waveforms of each lead sensed by an ECG sensing device so that the sensed ECG leads are aligned when displayed as are the waveforms in a traditional ECG tracing such as the exemplary one shown in FIG. 8. In some embodiments of the ECG sensing device, the ECG sensing device comprises a software application configured to time align two or more sensed ECG leads. In some embodiments of the ECG sensing device, a software application configured to time align two or more sensed ECG leads is a component of a system that receives data from an ECG sensing device.

When first and second electrodes of the ECG sensing device described herein are contacted by the right and left upper extremities of the user at the same time that a third electrode of the device contacts any one of the six precordial lead positions, a lead I is sensed simultaneously along with a sensed precordial lead. That is, lead I is equal to a voltage sensed at the left upper extremity minus a voltage sensed at the right upper extremity, so when left upper extremity, right upper extremity, and chest are all respectively contacted by an electrode of the ECG sensing device described herein, a lead I is sensed in addition to a precordial lead. Therefore, when all six precordial leads are sensed sequentially, six respectively corresponding "precordial lead I recordings"

are also generated: V1-lead I, V2-lead I, V3-lead I, V4-lead I, V5-lead I, and V6-lead I. Each of these six precordial lead I recordings is used to time align each of the precordial leads to the limb leads and thus time aligns precordial leads.

In some embodiments of the software application described herein, the software application aligns the precordial leads V1, V2, V3, V4, V5, and V6 by taking advantage of there being precordial lead I recordings sensed simultaneously with each of the V1, V2, V3, V4, V5, and V6 waveforms. That is, the precordial lead I recordings V1-lead I, V2-lead I, V3-lead I, V4-lead I, V5-lead I, and V6-lead I are each respectively time aligned with a precordial lead recording with which they are simultaneously sensed. Each of the precordial lead I recordings is time aligned with the lead I that is sensed along with the limb leads, by, for example, moving the precordial lead I recording a certain distance along the Y-axis, and because each of the precordial lead I recordings is time aligned with a precordial lead, each of the respective precordial leads V1, V2, V3, V4, V5, and V6 will also be time aligned when moved the same distance along the Y-axis as their co-sensed precordial lead I recording. For example, "V1-lead I" is a lead I recording that is time aligned with V1. "V1-lead I" is not the same as "lead I," which is the lead I recorded simultaneously sensed with the other five limb leads using the ECG sensing device described herein. "V1-lead I" is also not necessarily time aligned with "lead I" as these two different lead I recordings are not typically sensed simultaneously using the ECG sensing device described herein. Because, however, "V1-lead I" and "lead I" are both lead I recordings, they can be time aligned in a fairly straightforward manner as they would both be expected, when averaged, to have very similar (if not identical) morphology and timing between waveforms. For example, if the peak of the R wave of an averaged "lead I" occurs at 1 second, and the peak of the R wave of an averaged "V1-lead I" occurs at 1.5 seconds, the averaged "V1-lead I" will be re-positioned or shifted 0.5 seconds along the Y-axis so that the peak of its R wave occurs at 1 second as it does in in the averaged "lead I." Because V1 is time aligned with V1-lead I, it too must be shifted 0.5 seconds along the Y-axis in order to time align it with the averaged "lead I." When V1 is time aligned with "lead I," it will also be time aligned with the other five limb leads that are already time aligned with "lead I." A similar alignment occurs with V2, V3, V4, V5, and V6 by respectively aligning V2-lead I, V3-lead I, V4-lead I, V5-lead I, and V6-lead I with "lead I."

An exemplary time alignment method is as follows: The value of RA which is sensed at the right upper extremity may be set to 0 at any step within the following exemplary process. In a first step, the six limb leads are sensed as described herein when a user contacts a first electrode with a right upper extremity, a second electrode with a left upper extremity, and a third electrode with a left lower extremity. In this first step, the six sensed limb leads I, II, III, aVR, aVL, and aVF are time aligned by virtue of being sensed simultaneously. In a second step, the precordial leads are sensed sequentially as described herein wherein a first electrode of the device contacts a right upper extremity, a second electrode of the device contacts a left upper extremity, and a third electrode of the device sequentially contacts each of the six precordial chest positions CP1, CP2, C3, C4, CP5, and CP6. In a third step, the limb leads are averaged and as described (lead $I_{Average}$+lead $II_{Average}$)/3 generates a $WCT_{Average}$. In a third step, the electric potentials respectively sensed at CP1, CP2, CP3, CP4, CP5, and CP6 are each averaged. In a fourth step, $WCT_{Average}$ is used to generate the precordial lead values V1, V2, V3, V4, V5, and V6, as described, by subtracting $WCT_{Average}$ from each of the averaged electric potentials sensed at CP1, CP2, CP3, CP4, CP5, and CP6. In a fifth step, the precordial lead I recordings are each averaged. In a sixth step, the average precordial lead I recordings are each used to time align each of their respective co-sensed precordial leads V1, V2, V3, V4, V5, and V6 with lead $I_{Average}$. While in this exemplary method, the time alignment process is described as a series of steps, it should be understood that the steps described do not necessarily occur sequentially as at least some steps may occur in parallel nor do they necessarily occur in the order in which is described herein as at least some of the steps may occur in a different order. Likewise, it should be understood that one or more steps may be omitted or modified while still achieving the end point of the method which is a time alignment of one or more ECG leads sensed with an ECG sensing device as described herein. Thus, aligning any one of the precordial lead I recordings with lead $I_{Average}$ will provide an alignment of the associated precordial lead.

Analysis

Figure 9A:
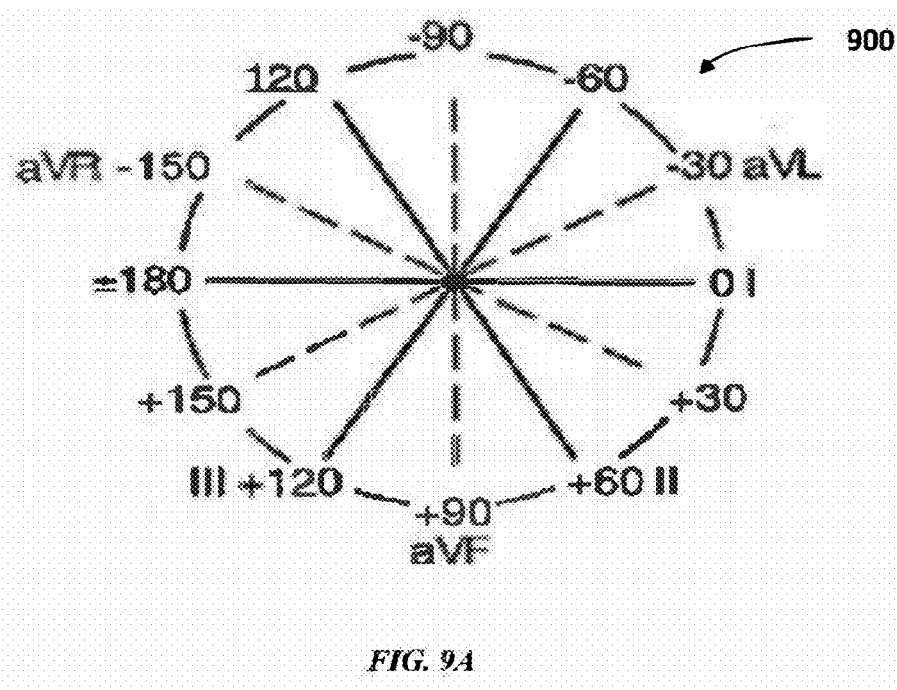
FIG. 9A shows an exemplary reference system 900 referred to as the Hexaxial Reference System and FIG. 9B shows an exemplary graphic representation of a QRS axis superimposed on the Hexaxial Reference System shown in FIG. 9A.

FIG. 9A shows an exemplary reference system 900 referred to as the Hexaxial Reference System as generated by some embodiments of the devices, systems, and methods described herein. The six sensed leads I, II, III, aVR, aVL, and aVF sensed by the ECG sensing device view the heart in the frontal plane, with each of the six leads corresponding to essentially a different angle view within the frontal plane of the heart based on the positions of the poles that correspond to the respective leads. Because the limb leads and the augmented limb leads are in the same plane, the positions of the different poles used to generate these six leads may be graphed in the two dimensions of the frontal plane. When represented in this manner, the six leads I, II, III, aVR, aVL, and aVF may each be represented on one of 12 lines separated by 30 degrees.

The Hexaxial Reference System shown in FIG. 9A is based on the spatial relationship of the poles of the six frontal plane leads I, II, III, aVR, aVL, and aVF to each other and the heart. More specifically, the Hexaxial Reference System is a representation of the electric potential difference that is measured between a pair of points on the body that as a pair respectively correspond to each of leads I, II, III, aVR, aVL, and aVF. For example, lead I corresponds to the difference in potential difference between a first electrode placed on the right arm and a second electrode placed on the left arm. A representation of the electric potential difference that is measured between the right arm and the left arm to generate lead I is a line that travels horizontally from right to left on the Hexaxial Reference System. The other lines of the Hexaxial Reference System are generated in the same manner, with each line essentially comprising a linear representation of the electric potential difference between two poles that correspond to one of the six leads. The representations of the six leads on the Hexaxial Reference System are assigned to six of the twelve different angles from the horizontal. For example, as shown in FIG. 9A, the representation of lead I is at 0 degrees. For example, as shown in FIG. 9A, the representation of lead aVR is at −150 degrees. The positons of the various leads on the Hexaxial Reference System as well as the angles that they represent is important in determining the QRS axis.

Figure 9B:
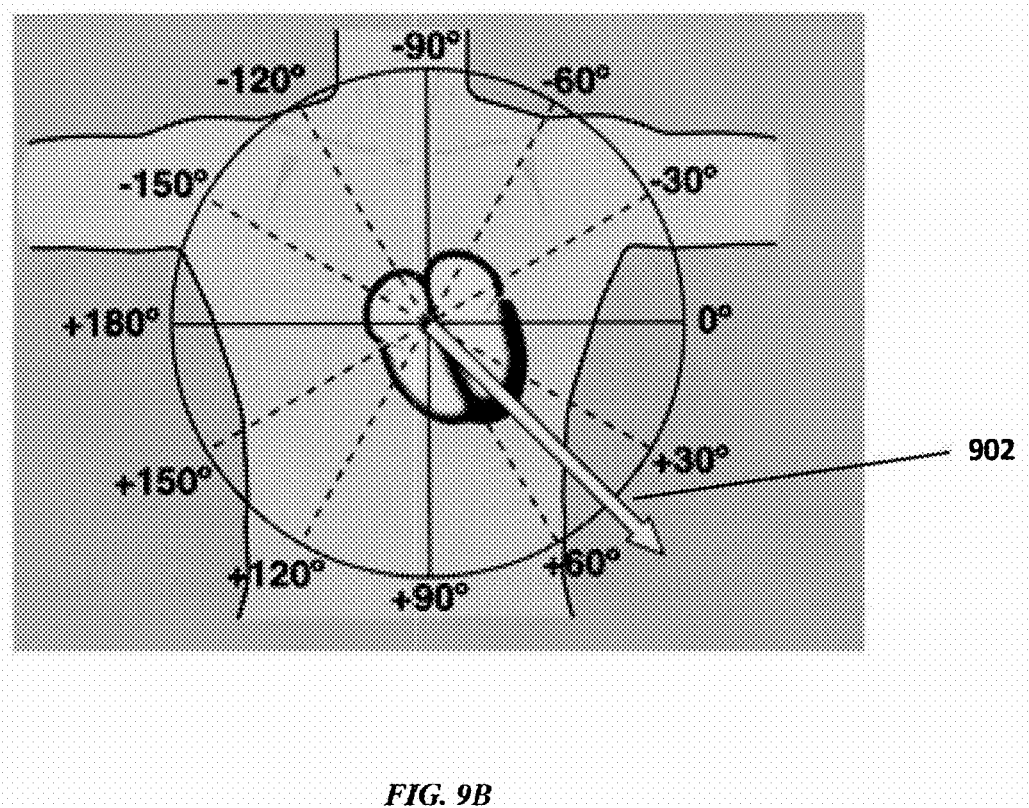

FIG. 9B shows an exemplary graphic representation of a QRS axis superimposed on the Hexaxial Reference System shown in FIG. 9A as generated by some embodiments of the devices, systems, and methods described herein. The QRS axis is an ECG based measure that provides information on the dynamics and structure of specific portions of the heart. The QRS axis refers to the general direction of the heart's depolarization wave front in the frontal plane during the duration of the QRS complex. Said in another way, the QRS axis comprises the mean electric vector in the frontal plane of the heart during ventricular depolarization.

In some embodiments of the devices systems and methods described herein, an ECG sensing device or system comprises a processor that runs software configured to generate a Hexaxial Reference frame and determine a mean electric vector from a sensed ECG that comprises a QRS axis. Each of the frontal leads I, II, III, aVR, aVL, and aVF has a vector associated with their respective QRS complexes. Each of the six lead vectors comprises a magnitude corresponding to the amplitude of the respective QRS complexes and a direction corresponding to the position of the respective lead on the Hexaxial Reference System. For example, when a lead I sensed by the ECG sensing device is determined to have a QRS complex having a positive amplitude, it is represented by a vector traveling along the 0 degree line of the Hexaxial Reference System with a magnitude corresponding to the amplitude of the QRS complex on lead I of the recorded ECG. In this embodiment, software determines a magnitude of each of the six lead vectors based on the amplitude of the QRS complexes of each of the six vectors, and a direction for each vector based on the positons of the leads on the Hexaxial Reference System and whether the QRS complex has a positive or negative deflection. The software then averages the six vectors to determine a mean frontal vector which comprises to a QRS axis.

In a normally conducting heart, the QRS axis typically lies in the direction of the largest muscular bulk in the heart, and in a normal heart, the area of the largest muscular bulk is the left ventricle, and thus the electric vector is typically directed from the right shoulder to the left leg. On the Hexaxial Reference System representation, a normal mean depolarization is said to be within −30 degrees and 90 degrees. If the mean depolarization vector varies beyond −30 degrees or 90 degrees, the user is said to have axis deviation. A deviation beyond −30 degrees is known as left axis deviation, and it means that there is a greater degree of electric activity in the left portion of the heart than there would be in a normal heart. A greater degree of electric activity than normal indicates an increase in muscular bulk in the left heart which is indicative of left ventricular hypertrophy. Similarly, a deviation beyond 90 degrees is known as right axis deviation, and it means that there is a greater degree of electric activity in the right portion of the heart than there would be in a normal heart. A greater degree of electric activity than normal indicates an increase in muscular bulk in the right heart which is indicative of right ventricular hypertrophy. Line 902 is a graphic representation of a QRS axis and it lies between 30 and 60 degrees. The software in this embodiment further determines whether a calculated mean electric vector has an angle and direction that is within normal range or corresponds to either left or right axis deviation. The software may be configured to display the QRS axis to a user or provide a warning if abnormal.

In some embodiments, the T-axis may be determined in the same way as the QRS axis, except that the vectors that are averaged to determine the T-axis are measured during the duration of the T-wave rather than during the QRS complex. That is, the T-axis refers to the general direction of the heart's depolarization wave front in the frontal plane during the duration of the T-wave. The T-axis comprises the mean electric vector in the frontal plane of the heart during the ventricular repolarization.

In some embodiments, software determines the difference between the vectors that respectively represent the QRS axis and T-axis, which is termed the frontal plane QRST angle. The frontal plane QRST angle has been demonstrated in multiple studies to be a predictor for cardiac death.

In some embodiments, software is configured to analyze an ECG to determine a heart rate variability. Heart rate variability is the physiological phenomenon of variation in the time interval between heartbeats. Typically, heart rate variability is measured by measuring the difference in time between successive R-waves. In this embodiment, software is configured to measures the time between R-waves on an ECG and monitor for changes in the time between R-waves. In some embodiments, the software continuously monitors heart rate variability. In some embodiments, the software intermittently monitors heart rate variability. In some embodiments, the software monitors heart rate variability when it is triggered to do so by, for example, a change in a biometric measured by a biometric sensor.

In some embodiments, software is configured to analyze an ECG to determine a QT interval and a corrected QT interval. The QT interval is a measure of the time between the start of the Q wave and the end of the T wave in the heart's electric cycle. The QT interval represents electric depolarization and repolarization of the ventricles. A lengthened QT interval is a marker for the potential of ventricular tachyarrhythmias like Torsades de Pointes and a risk factor for sudden death. A corrected QT interval accounts for the fact that heart rate changes create QT interval changes. A number of formulas are suitable for determining a corrected QT interval including Bazzett's formula which is expressed as corrected $QT=QT/\sqrt{RR}$. Typically, the QT is corrected using the preceding RR interval.

As explained, the QRS axis, T-axis, and QRST angle are importantly all derived from the six limb leads I, II, III, aVR, aVL, aVF that are sensed by the methods, systems, and devices described herein. In a typical ECG ten electrodes are placed on the skin surface of an individual in order to generate a 12 lead ECG, however, extremely valuable diagnostic information may be obtained through the six leads described alone. As stated, unlike the traditional 12 lead ECG which typically requires placement of 10 electrodes, a six lead ECG may be achieved with only three electrodes. The use of seven fewer electrodes than a traditional ECG is advantageous because it allows for the electrodes to conveniently be incorporated into or coupled with a mobile computing device making the ECG portable, whereas a traditional ECG is not easily portable. The devices and systems described herein allow an individual to conveniently record their own ECG, whereas in a traditional ECG the number of electrodes and their positioning on the body typically requires that a second person record the ECG. The devices and systems described herein may record an ECG on an individual quickly and easily while either sitting or standing, while traditional ECGs typically require an individual to lay supine or nearly supine and take some time to set up and record.

The systems, devices, and methods described herein comprise mobile computing devices with three electrodes that measure and display one or more leads of a 12-lead ECG along with determining one or more of a PR interval, a QRS duration, a frontal QRS axis, a frontal T-wave axis, a frontal P-wave axis, a frontal QRS-T angle, a QT interval, a corrected QT interval, a T-peak to T-end interval, a rhythm analysis, and an HRV analysis.

In some embodiments, an ECG sensing system comprises three electrodes coupled with a mobile computing device. The electrodes may be directly integrated into the mobile computing device. For example, the electrodes may be directly embedded in the housing of a mobile computing device such as, for example, a smartphone. That is, electrodes may be components of a mobile device such as, for example, a smartphone, a tablet computer, or a laptop computer. In this embodiment, ECG sensing electrodes are directly incorporated into the housing of a mobile computing device, and may, for example, be directly coupled, through a hardwire connection, to the hardware of the mobile computing device. For example, a smartphone processor may be directly hardwired to ECG sensing electrodes that are embedded within the housing of the smartphone.

In some embodiments, one or more electrodes may be external to the mobile computing device. In such an embodiment, the one or more external electrodes are wirelessly or hardwire coupled to a mobile computing device. Non-limiting examples of wireless connections may comprise, for example, a WiFi connection between the one or more external electrodes and the device, a BlueTooth connection between the one or more external electrodes and the device, a low power BlueTooth connection between the one or more external electrodes and the device, an NFC (near field communication) connection between the one or more external electrodes and the device, or a near field ultrasound communication connection between the one or more external electrodes and the device. It should be understood by those having knowledge in the art that other means of communicating wirelessly with a device are suitable for use with the systems, devices, and methods described herein.

In some embodiments, one or more electrodes is positioned on a protective case of a mobile computing device. In such an embodiment, the one or more electrodes is configured to communicate wirelessly with a receiver on the mobile computing device. For example, the one or more electrodes on a case of mobile computing device may transmit an ECG signal to a receiver on a mobile computing device using a Bluetooth signal.

ECG sensing electrodes sense an ECG signal by measuring an electric potential difference between two points on the skin surface of an individual. When a first electrode is in contact with a right hand of an individual and a second electrode is in contact with a left hand of an individual, a lead I recording may be generated, which comprises a graphic representation of an electric potential difference between the right and left hands over time. When a third electrode is added to the electrodes that respectively contact the right and left hands, the remaining five limb leads may be generated. For example, in an ECG sensing device with three electrodes, the first electrode is configured to contact a right hand, the second electrode is configured to contact a left hand, and a third electrode is configured to contact a left leg. When all three electrodes of the ECG sensing device are contacted at once, a lead I, a lead II, and a lead III are generated. Lead I is the potential difference between the electrode in contact with the left hand and the electrode in contact with the right hand. Lead II is the potential difference between the electrode in contact with left leg and the electrode in contact with the right arm. Lead III is the potential difference between the electrode in contact with the left leg and the electrode in contact with the left arm. Simultaneously, unipolar leads aVR, aVL, and aVF may be determined using the recorded leads I, II, and III as described above. Thus, using only three electrodes as described herein, all six of the limb leads may be generated.

In some embodiments, an ECG sensing device comprises three electrodes that are placed so as to conveniently contact a particular portion of the skin surface of an individual. For example, one electrode is positioned to contact the right hand of an individual, one electrode is positioned to contact the left hand of an individual, and a third electrode is positioned to contact the left leg of an individual.

Additionally, software incorporated with any of the systems, devices, methods described herein may be configured to analyze ECG data received from an ECG sensing device or an ECG sensing watch or wristlet. Analysis may comprise generating a QRS axis and a T axis value using the six leads I, II, III, aVR, aVL, and aVF as described herein.

Additionally, software incorporated with any of the systems, devices, methods described herein may determine a QRST angle by calculating the difference between the QRS axis and T axis as described herein.

Analysis may further comprise a rhythm analysis which may comprise determining a heart rate variability, a QT interval, or a corrected QT interval.

Additionally, software incorporated with any of the systems, devices, methods described herein may be used to determine a diagnosis or abnormality associated with an ECG. For example, as described an axis deviation may be associated with the abnormality of right or left ventricular hypertrophy. For example, heart rate variability may be associated with the diagnosis of atrial fibrillation. For example, QT interval changes may indicate certain arrhythmias.

Any of the systems, devices, and methods described herein may also be combined with sensors that measure physiologic parameters. For example, and of the systems, devices, or methods described herein may be incorporated with a blood pressure sensor. For example, any of the systems, devices, or methods described herein may be incorporated with a photoplethysmogram (PPG) sensor. For example, any of the systems, devices, or methods described herein may be incorporated with a temperature sensor. For example, any of the systems, devices, or methods described herein may be incorporated with a pulse oximetry sensor. For example, any of the systems, devices, or methods described herein may be incorporated with an accelerometer. Those having skill in the art will understand that other sensors that monitor or detect physiologic parameters are suitable for use with the systems, devices, and methods described herein.

In some embodiments, sensed physiologic data is transmitted to a processer in any of the systems, devices, and methods described herein. Software that is combined with any the systems, devices, and methods described herein may use said physiologic data that is sensed in combination with a sensed ECG to perform an analysis. For example, blood pressure data may be combined with ECG data by said software to provide an analysis that determines the presence of a ventricular tachycardia, an immediately life threatening condition.

The systems, devices, and methods described herein may include either or both of transmitters and receivers for transmitting and receiving wireless signals.

In some embodiments, software described herein also causes the transmission of a signal to a server when an abnormal analysis result is determined. For example, an abnormal analysis result comprises an abnormal ECG. For example, an abnormal analysis result comprises an abnormal QRS axis. For example, an abnormal analysis result comprises an abnormal QRST angle. In some embodiments, an abnormal analysis result comprises an abnormal ECG. For example, an abnormal analysis result comprises an abnormal heart rate variability value. Fr example, an abnormal analysis result comprises an abnormal physiologic parameter value. The transmitted signal may comprise a signal to an emergency care provider. For example, if an immediately life threatening condition is determined such as, for example, a VT the software described herein may send an emergency signal to a 911 operator, emergency care providers (e.g. paramedics), or other third party monitors.

In a fifth step, a six lead ECG is displayed on said display screen, said six lead ECG comprising said lead I, said lead II, said lead III, said lead aVR, said lead aVL, and said lead aVF.

While preferred embodiments of the systems, devices, and methods described herein have been shown and described herein, it will be obvious to those skilled in the art that such embodiments are provided by way of example only. Numerous variations, changes, and substitutions will now occur to those skilled in the art without departing from the user matter described herein. It should be understood that various alternatives to the embodiments of the systems, devices, and methods described herein may be employed in practicing the systems, devices, and methods described herein. It is intended that the following claims define the scope of the invention and that methods and structures within the scope of these claims and their equivalents be covered thereby.

What is claimed is:

1. An apparatus comprising:
a set of electrodes positioned on a housing to make contact with a set of limbs of a user, wherein the set of electrodes includes a left leg electrode to make contact with a left leg of the user; and
a processor operatively coupled to the set of electrodes, the processor configured to:
perform, using the set of electrodes, an electrocardiogram (ECG) to generate a set of limb leads including a first lead I;
determine a Wilson's Central Terminal (WCT) value using a subset of the set of limb leads;
in response to the left leg electrode of the set of electrodes contacting the user's chest:
generate a precordial lead based on electric potentials sensed by the left leg electrode while contacting the user's chest and the WCT value; and
as the precordial lead is generated, simultaneously generate a corresponding second lead I; and
time align the set of limb leads and the precordial lead using the second lead I to generate a time-aligned ECG.

2. The apparatus of claim 1, wherein the left leg electrode contacts the user's chest at a chest position where the precordial lead may be measured, and wherein to generate the precordial lead, the processor is configured to:
at the chest position where the precordial lead may be measured, generate the precordial lead based on a difference between an electric potential sensed by the left leg electrode at the chest position and the WCT value.

3. The apparatus of claim 2, wherein each of the set of limb leads, the electric potential sensed by the left leg electrode at the chest position, the second lead I, and the WCT value all comprise an averaged waveform, and wherein the precordial lead is generated by subtracting the WCT value averaged waveform from the electric potential averaged waveform sensed by the left leg electrode at the chest position.

4. The apparatus of claim 1, wherein the set of electrodes further includes a first electrode and a second electrode, the first electrode and the second electrode configured to make contact with a left hand and a right hand of the user respectively, and wherein the set of limb leads include the lead I, a lead II, and a lead III.

5. The apparatus of claim 1, wherein to time align the set of limb leads and the precordial lead, the processor is configured to:
determine a time at which a peak of an R wave of the lead I occurs;
determine a time at which a peak of an R wave of the corresponding second lead I occurs;
determine a difference between the time at which the peak of the R wave of the lead I occurs and the time at which the peak of the R wave of the corresponding second lead I occurs; and
shift, by the difference, the time at which the peak of the R wave of the corresponding second lead I occurs.

6. The apparatus of claim 1, further comprising a display, and wherein the processor is further configured to:
generate an ECG tracing comprising the time aligned ECG, wherein the ECG tracing comprises an x-axis corresponding to time and a y-axis corresponding to voltage.

7. The apparatus of claim 6, wherein the processor is further configured to:
generate a T axis based on the one or more limb leads; and
generate a QRST angle by calculating a difference between the QRS axis and the T axis.

8. The apparatus of claim 1, wherein the processor is further configured to:
generate a QRS axis based on an amplitude of a QRS complex of each of the one or more limb leads.

9. The apparatus of claim 1, wherein the housing comprises a wearable computing device.

10. The apparatus of claim 1, wherein the housing comprises a mobile computing device.

11. A method comprising:
performing, using a set of electrodes disposed on a housing, an electrocardiogram (ECG) of a user to generate a set of limb leads including a first lead I;
determining a Wilson's Central Terminal (WCT) value using a subset of the set of limb leads;
in response to a left leg electrode of the set of electrodes contacting the user's chest:
generating a precordial lead based on electric potentials sensed by the left leg electrode while contacting the user's chest and the WCT value; and
as the precordial lead is generated, simultaneously generating a corresponding second lead I; and
time aligning the set of limb leads and the precordial lead using the second lead I to generate a time-aligned ECG.

12. The method of claim 11, wherein the left leg electrode contacts the user's chest at a chest position where the precordial lead may be measured, and wherein generating the precordial lead comprises:
at the chest position where the precordial lead may be measured, generating the precordial lead based on a difference between an electric potential sensed by the left leg electrode at the chest position and the WCT value.

13. The method of claim 12, wherein each of the set of limb leads, the electric potential sensed by the left leg electrode at the chest position, the second lead I, and the WCT value all comprise an averaged waveform, and wherein generating the precordial lead comprises subtracting the WCT value averaged waveform from the electric potential averaged waveform sensed by the left leg electrode at the chest position.

14. The method of claim 11, wherein the set of electrodes further includes a first electrode and a second electrode, the first electrode and the second electrode configured to make contact with a left hand and a right hand of the user respectively, and wherein the set of limb leads include the lead I, a lead II, and a lead III.

15. The method of claim 11, wherein time aligning the set of limb leads and the precordial lead comprises:
   determining a time at which a peak of an R wave of the lead I occurs;
      determining a time at which a peak of an R wave of the corresponding second lead I occurs;
      determining a difference between the time at which the peak of the R wave of the lead I occurs and the time at which the peak of the R wave of the corresponding second lead I occurs; and
      shifting, by the difference, the time at which the peak of the R wave of the corresponding second lead I occurs.

16. The method of claim 15, further comprising:
   generating a T axis based on the one or more limb leads; and
   generating a QRST angle by calculating a difference between the QRS axis and the T axis.

17. The method of claim 11, further comprising:
   generating an ECG tracing comprising the time aligned ECG, wherein the ECG tracing comprises an x-axis corresponding to time and a y-axis corresponding to voltage.

18. The method of claim 11, further comprising:
   generating a QRS axis based on an amplitude of a QRS complex of each of the one or more limb leads.

19. The method of claim 11, wherein the housing comprises a wearable computing device.

20. The method of claim 11, wherein the housing comprises a mobile computing device.

* * * * *